United States Patent
Fareed

Patent Number: 5,642,739
Date of Patent: Jul. 1, 1997

[54] MAGNETIC ARM BAND FOR TENNIS ELBOW

[76] Inventor: Donald O. Fareed, 801 Buena Vista Ave., Santa Barbara, Calif. 93108

[21] Appl. No.: 669,580

[22] Filed: Jun. 24, 1996

Related U.S. Application Data

[63] Continuation-in-part of Ser. No. 441,985, May 16, 1995, abandoned, which is a continuation of Ser. No. 226,028, Apr. 11, 1994, abandoned.

[51] Int. Cl.⁶ ..................................................... A61F 5/37
[52] U.S. Cl. ............................ 128/881; 600/15; 128/878
[58] Field of Search .................................. 128/845, 846, 128/869, 878, 879, 881; 600/9–15; 602/20, 21

[56] References Cited

U.S. PATENT DOCUMENTS

| | | | |
|---|---|---|---|
| 3,841,306 | 10/1974 | Hallgren | 600/13 |
| 4,095,587 | 6/1978 | Ishikawa | 600/15 |
| 4,549,532 | 10/1985 | Baermann | 600/15 |
| 4,587,957 | 5/1986 | Castel | 600/9 |
| 4,727,857 | 3/1988 | Hörl | 600/9 |
| 4,798,194 | 1/1989 | Amishima | 600/15 |
| 5,067,940 | 11/1991 | Liboff | 600/15 |
| 5,152,302 | 10/1992 | Fareed | 602/13 |
| 5,226,020 | 7/1993 | Li | 600/9 |
| 5,304,111 | 4/1994 | Mitsuno | 600/15 |

*Primary Examiner*—Michael A. Brown
*Attorney, Agent, or Firm*—Michael G. Petit

[57] ABSTRACT

An adjustable strap or band adapted to be circumferentially fitted around a limb or other body portion to simultaneously, selectively compress and apply a magnetic field to target tissues in order to alleviate the symptoms of inflammation. The strap is a generally band-shaped device having inwardly protruding compression plates on its skin contacting surface to direct compression against the underlying soft tissue when the band is circumferentially tensioned and fastened in place around the affected body portion. In one preferred form, the band, adapted for treating tennis elbow, applies an adjustable pressure principally upon the extensor, supinator and flexor muscle wads permitting unimpeded blood circulation along all other portions of the forearm. Two opposing compression plates for applying transaxial compression are limited in their circumferential extent to those areas of the band immediately overlying the extensor and flexor muscle mass. The band has means thereon for applying a DC magnetic field to the underlying tissues while they are being compressed. In a preferred embodiment, the magnetic flux or field direction is orthogonal to the direction of blood flow through the inflamed tissues of the limb or body portion undergoing treatment.

5 Claims, 4 Drawing Sheets

MAGNETIC ARM BAND FOR TENNIS ELBOW

CROSS REFERENCE TO RELATED APPLICATIONS

This is a continuation-in-part of application Ser. No. 08/441,985; filed May 16, 1995 now abandoned, which is a continuation of 08/226,028; filed Apr. 11, 1994, now abandoned.

BACKGROUND OF THE INVENTION

1. Field of the Invention

The present invention relates generally to an adjustable compression band which simultaneously compresses soft tissue and applies a DC magnetic field thereto and, more particularly, to an arm band constructed to be worn by persons suffering from symptoms of lateral epicondylitis (tennis elbow), radial supinator syndrome and medial epicondylitis, carpal tunnel syndrome and similar overuse inflammatory conditions to relieve the symptoms thereof.

2. Reference to Copending Patent Applications

Reference is made herein to pending patent applications, Ser. No. 08/137,629, filed Oct. 15, 1993, entitled "Device and Method for Treating Carpal Tunnel Syndrome;" and Ser. No. 08/189,901, filed Feb. 1, 1994, entitled "Knee Compression Band," both by the present inventor.

3. Prior Art

Tennis elbow, sometimes referred to in the prior art alternatively as lateral epicondylitis or epicondylalgia externa, is frequently found in men and women between the ages of thirty and fifty who engage in racket sports. In people in the aforesaid age group, muscles and tendons become less supple and less able to absorb and dissipate the forces associated with sudden acceleration and deceleration which cause the inflammation associated with tennis elbow particularly where the extensor muscle mass meets the bone. Tennis elbow is also found in individuals pursuing activities such as golf and bowling. It is also found in certain trades such as carpentry, due to repeated hammering and driving of screws, and house painting, due to the forward and backward stroke of the brush.

Although "tennis elbow" is frequently thought of as an inflammation of the extensor muscles of the forearm, such inflammation may be accompanied by radial supinator inflammation due to repetitive pronation and supination. Such inflammation of the supinator muscle mass can cause tension on the overlying extensor muscle and resultant inflammation. The forearm extensor and supinator muscles are those that come into play during the extension, raising or snapping of the wrist. Every time a tennis ball hits a racket, there is a certain force or mechanical shock wave propagated up the forearm muscles which are already in tension due to the weight and acceleration of the racket and the tension caused by the centrifugal force of the stroke. If the ball is mis-hit, an extra force is added resulting in a snap of the wrist. It is this extra repetitive stress that causes the trauma leading to inflammation in the extensor and supinator muscles.

Prior art devices and procedures to control "tennis elbow" have been principally directed to lateral epicondylitis due to inflammation of the extensor muscle mass. Such devices include tension bandages for support and non-elastic bandages which are fastened around the forearm to inhibit the massive movement of the extensor and flexor muscles and absorb much of the shock. The following United States patents describe such devices and are made of record: U.S. Pat. Nos. 4,628,918; 4,905,998; 3,970,081; and 4,191,373.

Applegate, Jr., in U.S. Pat. No. 3,970,081 (referenced above) describes a support to be worn on the arm near the elbow joint for reducing pain in the elbow joint associated with the condition of tennis elbow. Applegate, Jr.'s strap comprises a tubular sleeve of one-way stretch fabric with an integral non-elastic strap. In use, the tubular sleeve is pulled up over the arm and positioned. The strap is tightened to compress a disc housed thereunder causing the disc to press against the forearm. Applegate, Jr. teaches positioning the tubular sleeve such that the compression disc underlying the inelastic band may be positioned on the arm wherever it will provide or afford the most relief. The Applegate, Jr. sleeve and integral band is substantially circular and because it is circular, it applies pressure substantially evenly about the forearm thereby impairing the circulation much like a tourniquet. It is, therefore, desirable to provide a pressure band similar to Applegate, Jr.'s without the disadvantage of impairing blood circulation in the forearm.

In U.S. Pat. No. 5,152,302, incorporated herein by reference, the present inventor describes the use of a device for applying transaxial compression to the flexor, extensor and supinator muscles of the forearm for alleviating the symptoms of tennis elbow. In a related copending application, the present inventor describes a device and method for treating the complex of symptoms generally referred to as carpal tunnel syndrome.

It is now well-established that the targeted application of controlled pressure to discrete areas of soft tissue can relieve inflammation. The above-referenced U.S. Pat. No. 5,152,302 patent teaches the use of such a band for treating tennis elbow while other copending applications teach the utility of applying controlled pressure to discrete or targeted portions of soft tissue to relieve tendonitis in the knee and carpal tunnel syndrome. It is important that the device employed does not exert a tourniquet effect or unduly interfere with blood flow in the affected limb.

Both AC and DC electric and magnetic fields have been employed to promote healing of fractured bones. Liboff, in U.S. Pat. No. 5,067,940 discloses a method and device for promoting cartilage growth by applying a fluctuating magnetic field to the cartilage, such field having a frequency determined by the magnetic field strength. The Liboff device (which is not adapted to be worn upon the body during periods of physical activity) provides a bidirectional alternating magnetic field superimposed on a constant, unidirectional magnetic field and means for permeating a cartilage with the composite magnetic field to encourage cartilage growth. Alternating DC magnetic fields have also been suggested for the treatment of soft tissue disease. For example, U.S. Pat. Nos. 4,758,429, 4,923,437, and 4,813,399 to Gordon describe a device and method of treating inflammatory joint disease or neuromuscular disease employing an external alternating magnetic field. In accordance with the teaching of the Gordon patents, magnetic dipoles are introduced into certain targeted effected cells and an external AC magnetic field applied. The intracellular dipoles, set in motion by the external field, destroy the cells.

Surprisingly, it has been found that the simultaneous application of a DC magnetic field and compression of discrete areas of inflamed targeted tissue act synergistically to reduce inflammation. The term "DC magnetic field" as used herein, refers to a continuous unidirectional magnetic field. It is, therefore, desirable to provide a compression band incorporating a permanent magnet which is useful for treating the symptoms of tennis elbow whether due to extensor, flexor or supinator inflammation. Additionally, the design of the band should minimally impair normal circulation up and down the arm.

SUMMARY OF THE INVENTION

The invention provides an adjustable band to be worn by a person or other mammal suffering from the symptoms of inflammatory disease associated with the overuse of a portion of the body comprising a means for applying pressure selectively to the affected soft tissue and, at the same time, applying a a unidirectional/non-fluctuating magnetic field having a constant field strength to the inflamed tissues of the effected limb. Surprisingly, it has been found that the application of a DC magnetic field to certain inflamed tissue, particularly tendons, in combination with the application of compression thereto promotes healing in many cases. It is an object of this invention to provide a magnetic compression band for use on a limb or other portion of the body of a mammal which can be employed to apply compression selectively to a target tissue in a body portion without substantially compressing non-target tissues.

It is still another object of this invention to provide a compression band for use around a limb or other body portion which applies a DC magnetic field to the target tissue contemporaneously with application of compression.

Another object of this invention is to provide a magnetic compression band with means thereon for selectively applying compression against an anatomically opposed pair of target tissues such as the extensor and flexor muscle wad where said countercompression means may be easily adjusted by the user while in use.

These and other objects of the invention will soon become apparent as we turn now to the drawings.

DESCRIPTION OF THE PREFERRED EMBODIMENT

Figure 1:
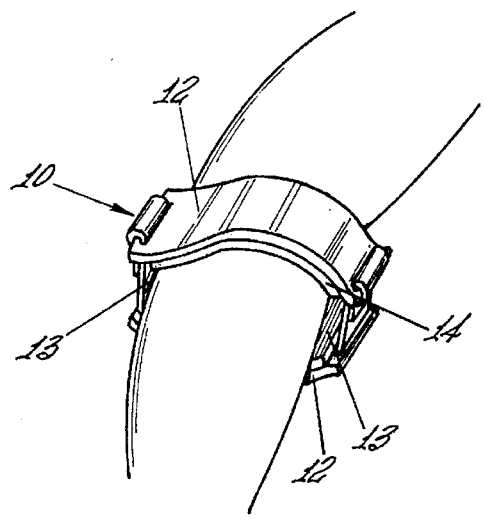
FIG. 1 is a perspective view of an embodiment of a prior art transaxial compression arm band circumferentially positioned on the arm of a person.

A compression band in accordance with the prior art is shown in FIG. 1. In FIG. 1, a band 10 is shown encircling the forearm 11. The band 10 has opposed compression plates 12 with inner skin-contacting surfaces 14 with discontinuities or gaps between the band 10 and the skin at 13. The positions of the discontinuities 13 are such that they overlie the non-target tissues to minimize pressure thereon and permit relatively unimpeded circulation of blood therethrough. When in use, the encircling band 10 may be positioned around the forearm to align the discontinuities 13 to overlie the non-target tissues of the forearm. The two opposing compression plates 12 (only one is clearly shown in FIG. 1) may then be positioned to overlie a target tissue such as the extensor and flexor muscle wads of the forearm and the band tightened. The presence of the discontinuities 13 around the inner circumference of the band space the band from the arm thereby permitting the unrestricted circulation of the blood while enabling the simultaneous transaxial compression of anatomically opposed muscle groups. A cross-sectional view of the prior art compression band encircling the forearm (FIG. 1) is shown in FIG. 2.

Figure 2:
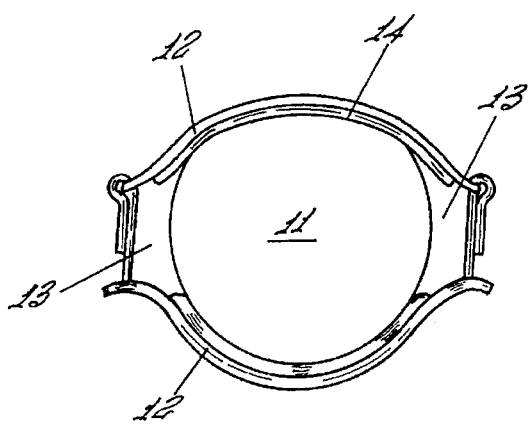
FIG. 2 is a from view of the prior art arm band of FIG. 1.
Figure 3:
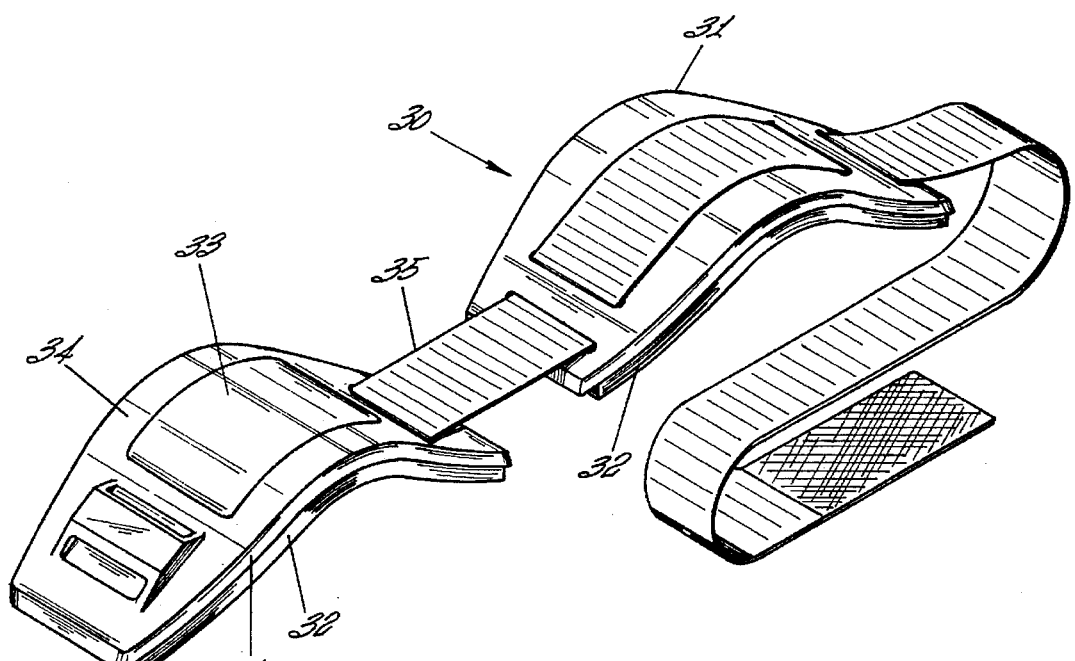
FIG. 3 is a perspective view of a preferred embodiment of a magnetic compression band according to the previous invention.

A modified embodiment of the prior art compression band of FIGS. 1 and 2 having at least one permanent magnet mounted thereon according to the teachings of the invention is shown in FIG. 3. The band, generally indicated at 30, has opposed compression plates 31, each plate having at least one flexible skin-contacting member 32 disposed on its inner surface. A permanent magnet 33 is affixed to outer surface 34 of the compression plates 31.

Figure 4A:
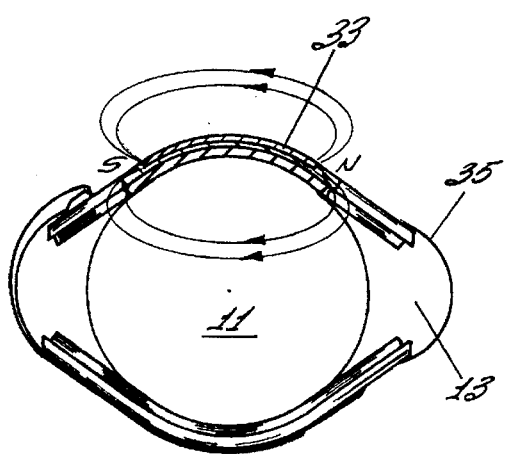
FIG. 4(a) is a cross-sectional view of the magnetic transaxial compression band having a single magnet positioned around the forearm.
Figure 4B:
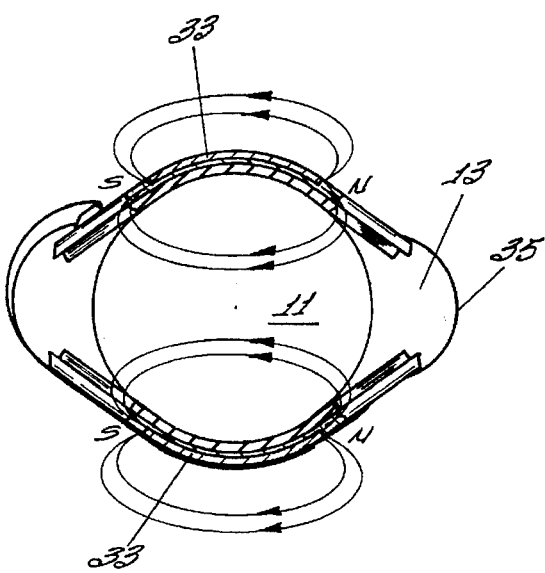
FIG. 4(b) is a cross-sectional view of the magnetic transaxial compression band having two magnets positioned around the forearm.

The construction of the band 30 is specially adapted to treat tennis elbow by providing transaxial countercompression to particular tissues as described in the '302 patent referenced earlier. The band 30 comprises two substantially "U" shaped flexible plates 31 linked to one another by one or more adjustable straps 35. The flexible plates 31 are semi-rigid but permit sufficient flexing or bending to enable the compression plate to conform to an anatomical surface. In the above embodiment, the inner skin-contacting surface 32 of one of the compression plates 31 may comprise one or more inflatable elastomer balloons (not shown), the pressure within the interior chamber of the balloons being adjustable by means of a finger-activated pump/exhaust as taught in the above-referenced '302 patent. Alternatively, or in combination with an inflatable member, the skin-contacting surface 32 of the compression plates 31 may be conveniently lined with a closed cell foam for comfort. When the strap 30 is securely fastened around the forearm with the opposing skin-contacting surfaces 32 overlying the extensor and flexor muscles, drawing the compression plates 31 together provides transaxial compression of the flexor, supinator and extensor muscles. A cross-sectional view of a forearm encircled with a magnetic compression band having a single magnet or a pair of magnets in accordance with the present invention is shown in FIGS. 4(a) and (b) respectively. The direction of the magnetic lines of flux are indicated by the arrowed lines. The flux lines preferably transect the axis of the forearm at right angles. In these embodiments (Fiures 4(a) and 4(b)) the magnet (S) 33 is/are placed below the compression band to position it/them close to the skin-contacting surface thereby increasing the magnetic field strength at the target tissue.

Figure 5:
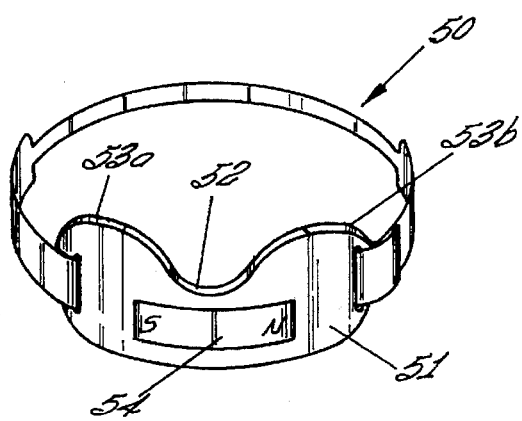
FIG. 5 is a perspective view of an embodiment of the magnetic compression band of the present invention adapted for the treatment of inflammation of the soft tissue of the knee.
Figure 7:
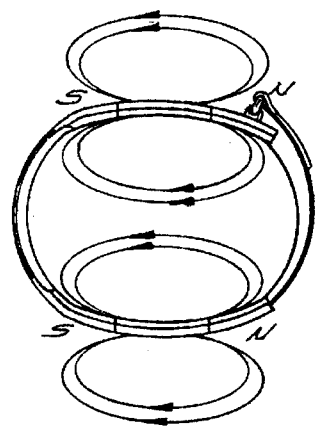
FIG. 7 is an axial plan view of the device of FIG. 6, the single-headed arrows showing the direction of the device-induced magnetic field at points in space relative to the position of the device.

While particular attention has been given to the use of a magnetic compression band for the treatment of tennis elbow, other applications are readily apparent. A knee magnetic compression band is indicated at 50 in FIG. 5. The band 50 has a single compression plate 51 with a notch 52 which rides below the patella. The upper lateral ridges 53a and 53b press against the soft tissue both lateral and medial to the patella. Magnets 54 are affixed to the band 50 to apply a DC magnetic field to the underlying tissue undergoing compression.

It is well know in electromagnetic theory that an axially symmetric DC magnetic field is produced by a direct, non-fluctuating electrical current circulating in one direction within a conductive ring. The axis of symmetry of the DC magnetic field is perpendicular to the plane of the circular current loop and passes through the center of the ring. A magnetic field produced by a permanent magnet has analogous field symmetry and properties and, for convenience, the terms "DC magnetic field" and "DC magnet" are used herein to describe a unidirectional, non-fluctuating magnetic field (or a magnet which produces a unidirectional, non-fluctuating magnetic field) having properties analogous to a DC magnetic field associated with a non-fluctuating DC current loop as described above. The term "unidirectional", as used herein to refer to a magnetic field, means that the magnetic field strength and direction at a point fixed in space relative to source of the magnetic field is constant and unvarying with time.

The magnet employed for the generation of a DC magnetic field may be an electromagnet but a permanent magnet is preferred. The permanent magnets may be disc-shaped, ring or donut shaped or any convenient shape which may be affixed to the compression band and generate a magnetic flux field preferably at right angles to the direction of blood flow through the portion of the body undergoing compression. The horizontal position of the single magnet 54 underlying notch 52 is presented for the purpose of illustration. A preferred embodiment of a knee band 50 includes two permanent magnets (not shown) vertically affixed to the compression plate 51 with like poles underlying the upper lateral ridges 53a and 53b. Flexible magnetic strips or sheets may be conveniently shaped into circular, oval or rectangular pieces and have the advantage of a low profile and are resistant to rusting. The choice of magnetic material depends on the desired field strength. Most commercially available materials such as Aluminum-Nickel-Cobalt (Alnico) Neodymium-Iron-Boron, Samarium-Cobalt, rare earth-cobalt and ferrite-based ceramic magnets are suitable for the purpose herein indicated. It is preferable to encapsulate the permanent magnet in a water impermeable coating to prevent corrosion.

Figure 6:
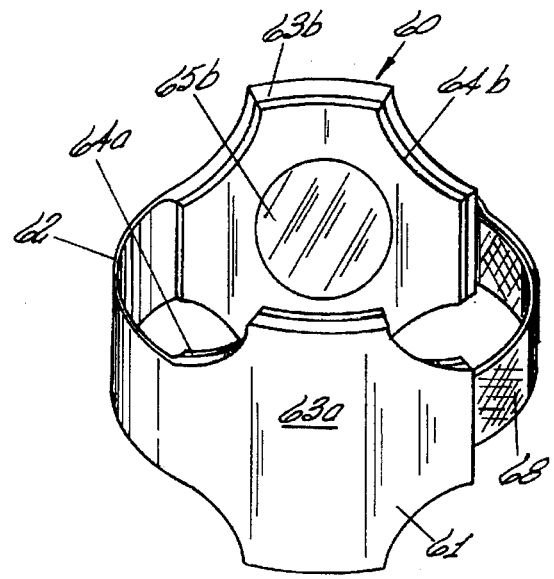
FIG. 6 is a perspective view of a particularly preferred embodiment of the invention wherein the transaxial compression band includes two anatomically opposed magnets disposed within the compression plate liners and recesses in the skin facing surface of the interconnected compression plates.
Figure 9:
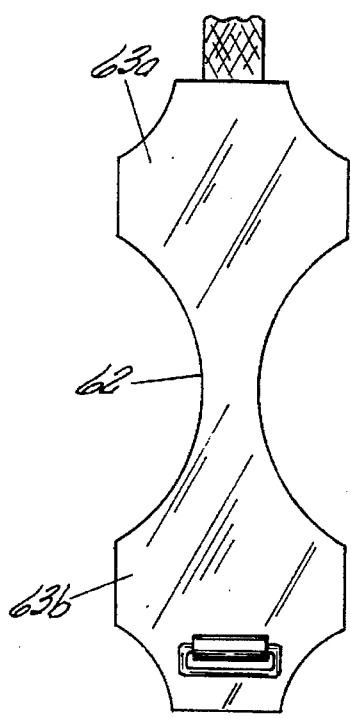
FIG. 9 is a top plan view of the device of FIG. 8.
Figure 8:
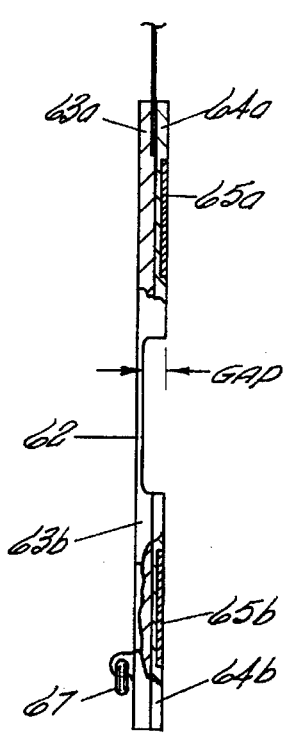
FIG. 8 is a partially cutaway side view of the embodiment of FIG. 6 showing the device with the band unfastened.
Figure 10:
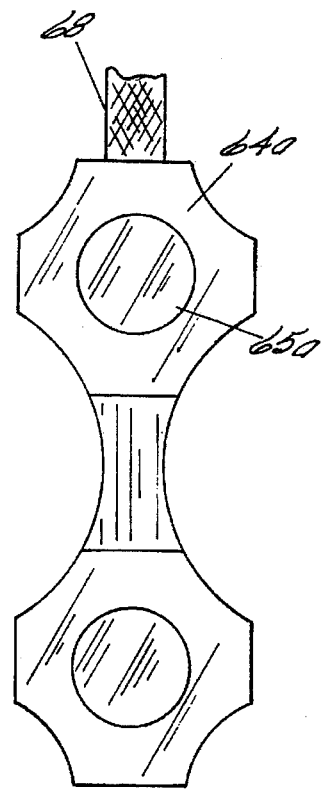
FIG. 10 is a bottom plan view of the device of FIG. 8.
Figure 11:
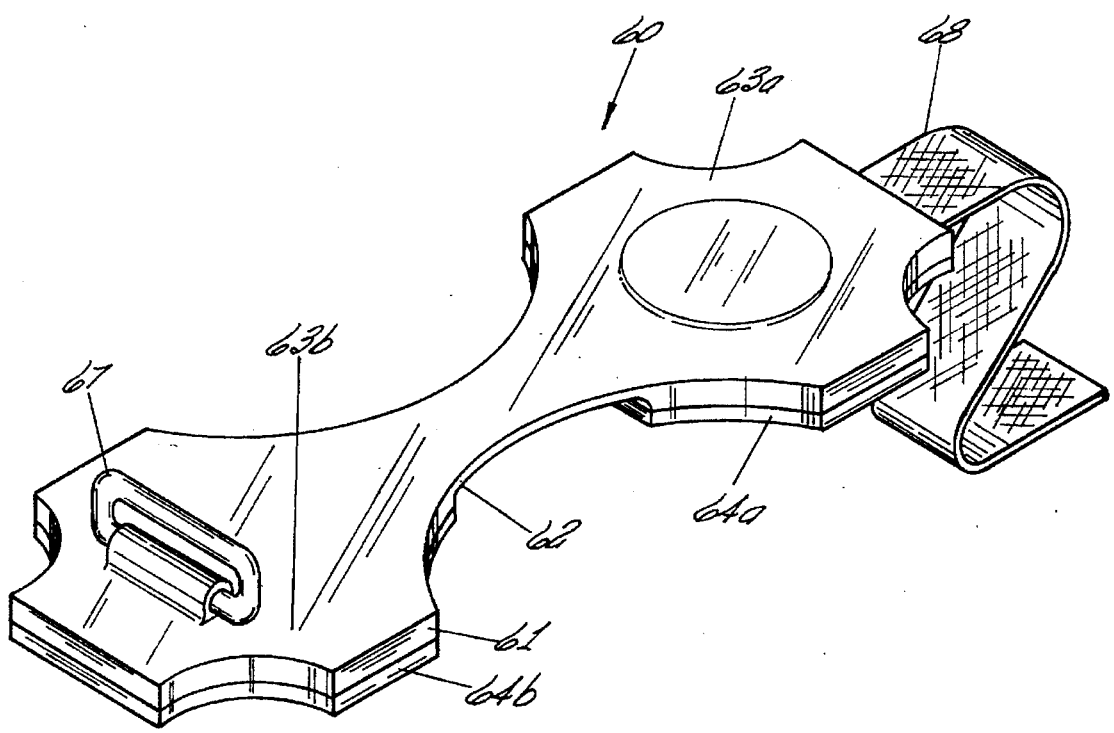
FIG. 11 is a perspective top view of the device of FIGS. 6 and 8.

A particularly preferred embodiment of a device for treating tennis elbow is shown in FIG. 6. The device 60 comprises a unitary elongate sheet of elastomer 61 having a central flexible waist portion 62 and extending laterally therefrom to form two compression plates 63a and 63b symmetrically disposed on opposing ends of the elastomer sheet 61 and having substantially identical bottom surfaces 64a and 64b. Identical sheets of a durable, resilient, slightly compressible closed-cell foam 67a and 67b are affixed to the skin-facing surfaces of the compression plates and serve to elevate the waist portion 62 above the skin and provide a gap therebetween to permit blood to circulate thereunder. The sheet 61 is symmetric with respect to the center of the flexible waist portion 62. One or more optional annular ridges 65a may be thermoformed in the upper surface of the compression plates 63a and/or 63b and dimensioned to snugly circumscribe and protect an identifying label affixed to the upper surface of the compression plate. A pair of identical recesses 65a and 65b in the foam layer and lower skin-facing surface of the compression plates 63a and 63b provide magnet attachment means and are dimensioned to snugly receive and stabilize a permanent magnet placed in the recess. A flexible strap 68 having a fixed end affixed to the surface of compression plates 63b, preferably to the upper surface thereof, and a free end. A "D"-ring 67 (not visible in FIG. 5) affixed to the upper surface of compression plate 63a is adapted to receive the free end of the flexible strap 68, the strap 68 including means adapted for securing the device 60 in encircling engagement around the forearm. The compression plates 63a and 63b and the thickness of the foam pads 64a and 64b affixed to the lower surfaces of the respective compression plates provides a gap between the waist portion 62 of the device and the underlying skin in the manner of the previously described embodiments.

In summary, the invention is a compression band for relieving the symptoms of inflammation by applying pressure to target tissue of the body while simultaneously applying a DC magnetic field to the inflamed target tissue. The combination of selectively applied pressure and a DC magnetic field act synergistically to relieve the symptoms associated with soft tissue inflammation. The magnetic transaxial compression arm band embodiment of the present invention is useful for treating the symptoms of tennis elbow. The band relieves the symptoms while having little adverse effect on circulation. The transaxial compression band minimizes the tourniquet effect.

It is to be understood that numerous modifications may be made in the illustrated preferred embodiment and other arrangements may be devised without departing from the spirit and scope of the invention as set forth in the appended claims. For example, the embodiment described herein for treating tennis elbow is exemplary and not to be interpreted as limiting. Simultaneous application of discrete pressure and a magnetic field to particular target tissue may be employed to treat other inflammatory conditions as well. While particular embodiments of the present invention have been illustrated and described it would be obvious to those skilled in the art that various other changes and modifications can be made without departing from the spirit and scope of the invention. It is therefore intended to cover in the appended claims all such changes and modifications that are within the scope of this invention.

What I claim is:

1. A device operable for treating inflamed soft tissue within a body extremity of a mammal consisting of:
   (a) a flexible band adapted to adjustably encircle and apply transaxial compression to a body extremity and comprising a flexible, nonextensible elastomeric sheet shaped to form two identical, relatively broad compression plates having a flexible, relatively narrow connecting portion therebetween, said compression plates having an arcuate concave skin-facing surface and a elastically deformable liner affixed thereto and coextensive therewith, each said liner having a recess therewithin and providing, in operation, means for elevating said narrow connecting portion above underlying skin, said band portion further comprising a flexible strap having a fixed end affixed to said upper surface of one of said means operable for adjustably and releasably fastening said band portion in an encircling position around the body extremity.

2. The device of claim 1 further comprising at least one permanent magnet disposed within said recess of said liner.

3. The device of claim 2 wherein said at least one permanent magnet is magnetic tape.

4. The device of claim 2 wherein said at least one permanent magnet is magnetic tape.

5. A device for treating inflamed soft tissue within a body extremity of a mammal consisting of:

(a) a flexible band adapted to encircle a body extremity and operable for exerting anatomically opposing pressure comprising two identical, relatively inflexible compression plates and a relatively flexible, elongate connection portion therebetween and affixed thereto, said length of said strap defining a space between said two compression plates, said compression plates each having arcuate concave skin-facing surfaces, each said skin-facing surface of said compression plate having a pad comprising a sheet of closed-cell foam elastomer affixed thereto, said foam pads having a skin-facing surface which are equal in area and coextensive with said skin-facing surface of each said compression plate, said flexible band further comprising a flexible attachment strap attached to one of said compression plates providing means operable for adjustably and releasably fastening said flexible band in an encircling position around the body extremity; and (b) a permanent magnet affixed to said band portion.

* * * * *